United States Patent [19]
von Gentzkow et al.

[11] Patent Number: 5,407,818
[45] Date of Patent: * Apr. 18, 1995

[54] BIOSENSOR CONTAINING A BIOCHEMICAL SUBSTANCE IMMOBILIZED ON A LAYER OF OLEFINIC-UNSATURATED, EPOXY FUNCTIONAL CROSS-LINKED POLYSILOXANE

[75] Inventors: Wolfgang von Gentzkow, Kleinsendelbach; Hans-Dieter Feucht, Renningen; Helmut Formanek, Garching; Gerhard Wanner, Moosburg, all of Germany

[73] Assignee: Siemens Aktiengesellschaft, Munich, Germany

[*] Notice: The portion of the term of this patent subsequent to Feb. 14, 2012 has been disclaimed.

[21] Appl. No.: 35,030

[22] Filed: Mar. 22, 1993

[30] Foreign Application Priority Data

Mar. 23, 1992 [DE] Germany .................. 42 09 367.8

[51] Int. Cl.$^6$ .................. C12M 11/08; C12M 1/40; G01N 27/26; C08G 77/04
[52] U.S. Cl. .................. 435/180; 435/12; 435/14; 435/25; 435/26; 435/27; 435/176; 435/288; 204/403; 528/25
[58] Field of Search .............. 435/174, 176, 180, 182, 435/288, 12, 14, 25, 26, 27; 204/403; 528/25

[56] References Cited

U.S. PATENT DOCUMENTS

| | | | |
|---|---|---|---|
| 3,844,892 | 10/1974 | Matthems | 195/68 |
| 3,852,708 | 12/1974 | Porath et al. | 195/68 |
| 4,612,288 | 9/1986 | Bigwood et al. | 435/180 |
| 4,894,253 | 1/1990 | Heineman et al. | 427/36 |

FOREIGN PATENT DOCUMENTS

0291130 11/1988 European Pat. Off. .
2656423 6/1991 France .

OTHER PUBLICATIONS

Hartmeier, W., "Immobilisierte Biokatalysatoren", Springer-Verlag Berlin, Heidelberg 1986, pp. 23-51.
Woodward, J., "Immobilized cells and enzymes", IRL Press, Oxford, Washington, D.C. (1985), pp. 3-54.
"Ber. Bunsenges. Phys. Chem.", vol. 92 (1988), pp. 1423-1426.
Nakamoto, S., et al., "A Lift-Off Method For Patterning Enzyme-Immobilized Membranes in Multi-Biosensors", Sensors and Actuators, vol. 13 (1988), pp. 165-172.
Tsukada, K., et al., "Long-Life Multiple-Isfets With Polymeric Gates", Sensors and Actuators, vol. 18 (1989), pp. 329-336.
Kuriyama, T., et al., "Development of Biosensors with Immobilized Enzyme", Chemical Economy & Engineering Review, vol. 17 (Aug. 1985), No. 7-8, pp. 22-27.
Hanazato, Y., et al., "Integrated Multi-Biosensors Based on an Ion-Sensitive Field-Efect Transistor Using Photolithographic Techniques", IEEE Transactions Electron Devices, vol. 36 (1989), pp. 1303-1310.
"Proc. 3rd Int. Conf. Solid State Sensors and Actuators (Transducers '85)", Jun. 11-14, 1985, pp. 148-151.
Derwent Abstract, 89-294709/41, Torres et al., EP-336854, Oct. 1989.

Primary Examiner—David M. Naff
Attorney, Agent, or Firm—Kenyon & Kenyon

[57] ABSTRACT

A biosensor is prepared having a selective detection system containing a biochemical substance such as an enzyme immobilized on an olefinic-unsaturated, epoxyfunctional polysiloxane. Prior to immobilization of the biochemical substance, the polysiloxane is applied as a layer to a carrier and cross-linked by treatment with high-energy radiation. A biochemical substance is reacted with epoxy groups of the cross-linked polysiloxane. Any non-reacted epoxy groups are reacted with a compound containing an amino group, a carboxyl group or an amino group and a carboxyl group to stabilize. After cross-linking and before reacting of the biochemical substance, the cross-linked polysiloxane can be hydrophilized by reacting some of the epoxy groups with a hydrophilic compound containing a reactive group.

3 Claims, No Drawings

BIOSENSOR CONTAINING A BIOCHEMICAL SUBSTANCE IMMOBILIZED ON A LAYER OF OLEFINIC-UNSATURATED, EPOXY FUNCTIONAL CROSS-LINKED POLYSILOXANE

FIELD OF THE INVENTION

The invention relates to biosensors with a selective detection system which includes a polymer and a biochemical substance, particularly an enzyme.

BACKGROUND OF THE INVENTION

Biosensors are chemosensors with a biological detection system. This detection system consists of biologically active substances, such as enzymes, antibodies, lectins, hormone receptors, etc., which are immobilized on the surface of the sensor or in a thin layer located on it. In the detection process, a change is produced on the surface or in this layer of the sensor, by interaction with the gaseous or liquid medium to be characterized, which can be evaluated using electrical, optical, mechanical, acoustical or calorimetric measurement methods. In the case of equipment with electronic data acquisition and evaluation, the active surface or layer is directly coupled, as a signal emitter, with a signal transformer, called a transducer, which is connected with the evaluation electronics for this purpose.

The reliability of the entire sensor depends on the assignability and reproducibility of the signals generated in the sensitive layer of the biosensor. This means that the layer must demonstrate not only high selectivity and sensitivity, but also a function that is free of hysteresis and drift, as well as chemical and biological stability and contamination resistance. For technical use, in particular, ease of operation, easy integration and the lowest possible measurement/regeneration time requirement are required, as well as great long-term stability. In addition, the production of the layer—according to methods which are efficient in terms of production technology and can be automated—should be as simple, reproducible and inexpensive as possible, and be such that it can be integrated into the production process for sensor production.

Until now, only such biosensors which are based on enzymatic reactions have achieved any practical importance. In these reactions the circumstance is used that products which can easily be detected, such as $H^+$, $O_2$, $H_2O_2$, $CO_2$ and $NH_3$, are formed or consumed. With regard to selectivity and sensitivity, the enzymatic reactions fully meet the requirements. But a difficulty exists in immobilizing the enzymes—without loss of activity—in as thin a detection layer as possible, in such a way that they are easily accessible for the substances to be detected, and are resistant to poisoning as well as biochemical pollutants, and remain functionally stable for as long as possible.

For the immobilization of enzymes, the following methods have been known:
- adsorption on carrier surfaces
- ionic binding to carrier surfaces
- covalent binding to carrier surfaces
- absorption in polymer layers
- inclusion in a polymer lattice (matrix sheathing, microencapsulation)
- inclusion by sheathing with a membrane (macroencapsulation)
- cross-linking or copolymerization with difunctional or polyfunctional monomers.

However, as is evident from the extensive literature on the immobilization of enzymes, all of these methods have disadvantages, which make them appear unattractive for industrial sensor production (see, for example: W. Hartmeier, "Immobilisierte Biokatalysatoren" ["Immobilized Biocatalysts"], Springer-Verlag Berlin, Heidelberg 1986, pages 23 to 51, as well as J. Woodward, "Immobilised cells and enzymes", IRL Press, Oxford, Washington D.C., 1985, pages 3 to 54).

Thus, adsorption and ionic binding of enzymes at the surface results in relatively unstable systems with a limited range of use: Changes in the pH and the ion intensity of solutions in contact with it, or the presence of other substances, already result in displacement of the surface-bound enzyme and thus to activity losses of the detection system. Also, in the case of absorption in polymer layers, with plasticized polyvinyl chloride being used in the predominant number of cases (see, for example: "Sensors and Actuators", Vol. 18 (1989), pages 329 to 336, and "Ber. Bunsenges. Phys. Chem." ["Reports of the Bunsen Society for Physical Chemistry"], Vol. 92 (1988), pages 1423 to 1426), relatively unstable systems are obtained: migration and extraction of the enzymes result in a constant decrease in activity (drift) and limit the lifetime of the sensor.

Significantly more stable systems are achieved if the enzymes are covalently bound to a carrier surface, made insoluble via cross-linking or copolymerization, or are immobilized by microencapsulation or macroencapsulation. For the formation of covalent bonds and for cross-linking, free amino, carboxyl, hydroxyl and mercapto groups are available on the part of the enzymes. Both inorganic materials, such as glass, and natural and synthetic organic polymers can be used as the carrier material. A prerequisite in this connection is that the carrier materials contain reactive groups, such as isocyanate, isothiocyanate, acid chloride and epoxy groups. Less reactive groups can be activated, for example carboxyl groups can be activated using the carbodiimide or azide method, hydroxyl groups can be activated using the bromine cyan method, and amino groups can be activated using the isothiocyanate or azo method. It was possible, particularly on the basis of acrylic acid and methacrylic acid derivatives, to produce numerous reactive copolymers with dinitrofluorophenyl, isothiocyanate, oxirane or acid anhydride groups. Polyacrylamides with oxirane groups as well as modified copolymers on the basis of vinyl acetate and divinyl ethylene urea with oxirane groups are commercially available, for example.

Immobilization by cross-linking or by copolymerization represent special forms of covalent binding. In these methods, the formation of covalent bonds takes place between the enzyme molecules and difunctional or polyfunctional monomers, such as glutardialdehyde, or, in the case of copolymerization, additionally between the enzyme molecules and a polymerizing substance. In this manner, insoluble aggregates with a high molecular weight are formed. Cross-linking is generally used as an immobilization method in combination with one of the other methods, for example in combination with adsorption or absorption. Here, the enzyme molecules are first adsorbed on the surface of the carrier, or are absorbed in a layer located on it, and subsequently cross-linked.

A significant disadvantage of immobilization by covalent binding is the great stress on the biocatalysts connected with it. The immobilization procedures that are necessary, some of which are rough, in which a strong change in the pH occurs, organic solvents have to be used or reaction with reactive substances with a low molecular weight takes place, almost always lead to strong conformation changes and thus to activity losses of enzymes bound in such manner.

In immobilization by inclusion, i.e. microencapsulation or macroencapsulation, the enzymes themselves are not made insoluble, rather their reaction range is limited by semipermeable polymers or polymer layers. A prerequisite for the ability of enzymes sheathed in this manner to function is that substrates and products can pass through the sheathing substance, while the enzymes themselves have to be held back. In addition to natural polymers, such as alginate, carrageenan, pectin, agar and gelatin, which are, however, too large-meshed for permanent immobilization of enzymes, synthetic polymers, such as polyacrylamide, are particularly used for matrix sheathing. Polyamides, polyurethanes, polyesters and polyureas, for example, are used for encapsulation. The inclusion method has the disadvantage that relatively thick layers with long sensor response times are formed.

In the methods described, immobilization of the enzymes is carried out by hand in most cases, which is relatively slow, expensive and not very reproducible, and is counter to integration into modern production processes. In view of the advantages which enzyme sensors on an FET basis (ENFETs) would be able to offer, attempts have been made in recent years to include enzyme immobilization into the planar technology in the production of integrated circuits. Thus, for example, the production and direct photo-structuring of layers based on polyvinyl alcohol which contain enzymes and can be photo-cross-linked has been described ("Proc. 3rd Int. Conf. Solid State Sensors and Actuators (Transducers '85)" Jun. 11–14, 1985, pages 148 to 151). For the purpose stated, it is also known to use photosensitive polyvinyl pyrrolidone "(IEEE Trans Electron Devices" Vol ED-36 (1989), pages 1303 to 1310). According to this method, structures which exactly cover the gates of the FETs can be produced on wafers. However, this method has the great disadvantage that the enzymes are at least partially inactivated during UV irradiation.

It is also known to utilize enzyme inactivation by means of UV radiation, in that first a layer of acetyl cellulose containing an enzyme is produced, the enzyme is cross-linked with glutardialdehyde in this layer, and subsequently it is irradiated through a mask in such a way that the gate coverings are shaded and therefore remain active, while the remaining areas are inactivated ("Chemical Economy & Engineering Review", Vol. 17 (1985), No. 7–8, pages 22 to 27). The inactivated layer remains on the sensor, which proves to be a disadvantage for further insulation and packaging of the sensor required for its use.

The lift-off technique has also been described ("Sensors and Actuators" Vol 13 (1988), pages 165 to 172). In this method, a photoresist is structured in such a way that only the gate surfaces remain free. The enzyme is then applied to this, together with glutardialdehyde, and cross-linked; the photo varnish is removed with acetone and ultrasound, using the lift-off technique. Here again, it is impossible to avoid at least partial denaturing of the enzyme.

SUMMARY OF THE INVENTION

It is an object of the invention to provide a biosensor with a selective detection system (composed of a polymer and a biochemical substance), which can be produced in technically simple, efficient and low-cost manner, where the production method is such that it can be integrated into modern production systems, and yields detection systems with stable functions, if necessary also miniaturized and integrated, with uniform quality and long life expectancy, in a reproducible manner.

This is accomplished, according to the invention by: applying an olefinic-unsaturated, epoxyfunctional polysiloxane to a carrier material in the form of a layer, cross-linking the polysiloxane to form a large-mesh epoxy-functional polymer matrix by means of high-energy radiation, treating the layer with an aqueous solution of the biochemical substance, whereby the biochemical substance is immobilized in the polymer matrix by reaction with epoxy groups, and stabilizing the layer by reaction of non-converted epoxy groups with a compound containing amino and/or carboxyl groups.

DETAILED DESCRIPTION OF THE INVENTION

The invention utilizes a new type of immobilization of enzymes and other biochemical substances with selective detection properties, specifically in layers of radiation-cross-linked epoxyfunctional polysiloxanes. It was surprisingly found that these substances are able to penetrate into large-mesh cross-linked epoxy-functional polysiloxanes—from aqueous solution—and can be anchored in the polymer matrix, i.e. in the polymer network, under very mild conditions, by reaction with epoxy groups in chain position. This fact is completely new, and it allows for the possibility of carrying out the production, structuring and cross-linking of the layers before immobilization of the biochemical substances, and thus of avoiding damage to the substances, most of which are very sensitive, by the processes mentioned.

The production of the detection system of the biosensor according to the invention includes the following steps, in general:

1. Layer preparation

An epoxyfunctional polysiloxane which can be cross-linked by radiation, or a mixture of such polysiloxanes, is applied, in the desired layer thickness, to a carrier material, if necessary in combination with a cross-linking initiator, a cross-linking reinforcer and/or other additives. Depending on the application case and the carrier material, this can be done out of a solution or without solvent, by dipping, spin-coating, roller-coating, curtain-coating or another conventional process, where it might be necessary to pretreat the carrier surface with an adhesion agent. The layer thickness can be controlled by adjusting the viscosity and by adding a solvent or a reactive diluent. The layer produced in this manner must be freed of volatile components, in every case, which can be done by drying or degassing, for example.

2. Cross-linking of the layer

Cross-linking of the layer, i.e. the polysiloxane, takes place by means of high-energy radiation, particularly UV, electron or γ radiation. In this connection, only the olefinic-unsaturated groups that can be polymerized by radicals are converted, while the epoxy groups are quantitatively maintained. As a result of the cross-linking, a large-mesh polymer network is formed. The layer can also be structured if projection exposure or irradiation through a mask and subsequent dissolution of the non-cross-linked regions is carried out.

3. Immobilization of the biochemical substance

Upon contacting of the cross-linked layer with an aqueous solution of the biochemical substance, this substance migrates into the polymer matrix and is covalently bound there by reaction with the epoxy groups. A prerequisite for this process, along with the necessary mesh width, is sufficient hydrophilicity of the polymer network formed during cross-linking. Immobilization can therefore be accelerated by prior hydrophilization of the polysiloxane. This is done by conversion of part of the epoxy groups with hydrophilic compounds which contain reactive groups, such as NH, OH, SH or COOH groups, causing the hydrophilic character of the polymer layer to be increased. The immobilization process can also be significantly accelerated by means of additives, such as polyvinyl pyrrolidone, which result in increased water absorption of the polysiloxanes, as well as by solvents which are miscible with water, such as dioxane, tetrahydrofuran, alcohols or polyethers. Furthermore, several different biochemical substances can also be immobilized in a single layer, and this can be done either simultaneously or consecutively.

4. Stabilization of the layer

This step includes the reaction of epoxy groups remaining after immobilization, with a compound containing amino and/or carboxyl groups, particularly an amino acid. Depending on the compound used, stabilization can be utilized to achieve closer cross-linking of the layer, and thus improved mechanical strength, or for adaptation of the material properties and the material transport. Furthermore, a superficial covering of the sensor layer with one or more additional layers is possible, which might also be practical for adjusting defined diffusion conditions.

For the biosensor according to the invention, epoxyfunctional polysiloxanes with the following structure are particularly suitable; these are the subject of the U.S. patent application Ser. No. 08/034,063, entitled "Polysiloxanes" which was filed on the same day as this application:

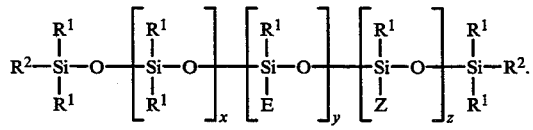

Here, the following applies:
E=epoxyfunctional remainder with 4 to 20 C atoms,
Z=vinyl group or photopolymerizable remainder with 8 to 40 C atoms, which can be obtained by addition of a photopolymerizable compound to a remainder E located at the siloxane chain, and subsequent addition of an aliphatic, cycloaliphatic or aromatic monoisocyanate or monoisothiocyanate with 2 to 10 C atoms to the secondary OH group formed upon opening of the epoxide ring,
$R^1$=alkyl with 1 to 4 C atoms or phenyl,
$R^2$=$R^1$, E or Z,
where the remainders $R^1$ and $R^2$ can be the same or different in each instance,
$x$=50 to 1000, $y$=10 to 300, $z$=3 to 8;
$x$ is preferably about 3 to 10 times $y$.

In the formula, the individual structural groups of the polysiloxanes are indicated in summary form; in fact, these groups are statistically distributed over the polymer chain.

The epoxyfunctional remainder E is preferably one of the following remainders:

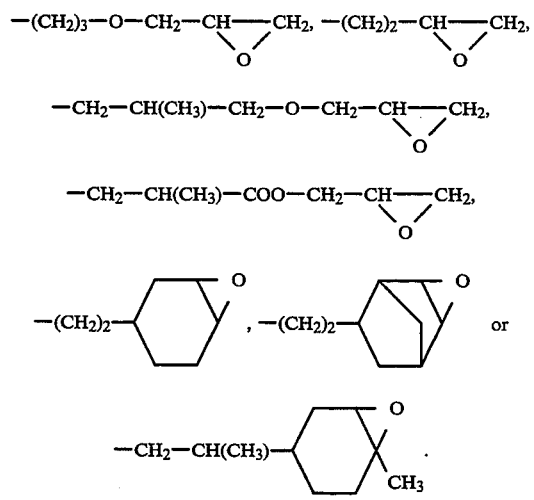

Photopolymerizable compounds, i.e., olefin-unsaturated compounds which are suitable for the reaction, with epoxy groups, i.e., with the remainder E, are particularly acrylic acid, methacrylic acid, hydroxyethyl acrylate, hydroxyethyl methacrylate, hydroxyethyl maleinimide, cinnamic acid, glycerol diacrylate and glycerol dimethacrylate. A suitable monoisocyanate is propyl isocyanate, for example.

Polysiloxanes of the type stated above which have vinyl groups are known from EP-OS 0 336 854. The epoxyfunctional polysiloxanes used in the invention are produced by reacting polysiloxanes having epoxy groups with an olefinic-unsaturated compound containing hydroxyl or carboxyl groups in a molar ratio of <1, with reference to the epoxy groups, and adding a monoisocyanate or monoisothiocyanate on the hydroxyl groups formed in this way.

The polysiloxanes with epoxy groups can be obtained by addition of epoxy compounds with an ω positioned C═C double bond to SiH-functional polysiloxanes. Suitable epoxy compounds are particularly allyl glycidyl ether, 2-methyl-allyl glycidyl ether, epoxy butene, methacrylic acid glycidyl ester, vinyl cyclohexene oxide, vinyl norbornene oxide and limonene oxide. The same or very similar polysiloxanes are also accessible by epoxidation of polysiloxanes with chain-positioned ω-alkenyl, ω-alkenyl ether and ω-alkenyl ester groups.

Olefinic-unsaturated compounds which are particularly suitable for the reaction with the epoxy groups of the polysiloxanes produced in the manner stated are acrylic acid, methacrylic acid, hydroxyethyl acrylate, hydroxyethyl methacrylate, hydroxyethyl maleinimide, cinnamic acid, glycerol diacrylate and glycerol dimethacrylate, or mixtures of these compounds. Acrylic acid and methacrylic acid, in particular, can also find use in a mixture with the corresponding anhydrides. The compounds according to the invention are obtained by reaction of the products formed by the addition of the olefinic-unsaturated compounds to the polysiloxanes which have epoxy groups, with monoisocyanate or monoisothiocyanate. In this reaction, the iso(thio)cyanates react with the vicinal hydroxyl group, which is formed by opening of the oxirane ring during the previous addition reaction. Preferably, propyl isocyanate is used as the monoisocyanate. Other possible compounds are, for example butyl isocyanate and phenyl isocyanate as well as propyl isothiocyanate and phenyl isothiocyanate.

The invention offers the following advantages:

Immobilization of all biochemical substances which have reactive NH, OH, SH or COOH groups at their periphery is made possible.

The layers which have the immobilized biochemical substances can also be stored dry and under non-sterile conditions, without any damage to these substances.

Immobilization of the biochemical substances takes place under very mild conditions, in aqueous solution and in the absence of reactive components with a low molecular weight; in this way losses, for example as the result of enzyme denaturing, are avoided.

A relatively small number of polymer materials with great chemical and thermal stability, which can be produced on a large technical scale and which are therefore accessible at low cost, is used for immobilization of a large number of different types of biochemical substances and for different sensor types.

The production and cross-linking of the layers, as well as their structuring, if necessary, can be carried out according to planar technology, i.e. in technically simple, reproducible and low-cost manner, and so as to be integrated into the sensor production.

Immobilization of the biochemical substances can take place independent of the layer production, depending on the need and intended use, if necessary not until just before use, to be carried out by the user.

Desorption, migration and extraction losses are avoided by chemical anchoring of the biochemical substances in the polymer matrix.

By the formation of covalent bonds between the peripheral NH, OH, SH and COOH groups of the biochemical substances and the very soft and flexible sheathing polymer material, the substances, some of which are very sensitive, for example enzymes, are given great functional and long-term stability.

Because of the possibility of the production of very thin layers ($<<1$ μm), very short sensor response times can be achieved.

Miniaturization and integration of the detection systems into microelectronic circuits, for example for the production of ISFETs and ENFETs, can be achieved without problems.

The selective detection systems are basically suitable for all sensor measurement arrangements.

The invention will now be explained in greater detail with reference to the following examples which should be regarded in an illustrative rather than a restrictive sense.

EXAMPLES 1 TO 5

Synthesis of polysiloxanes containing epoxy groups (polyepoxysiloxanes) as the starting compounds for the production of the epoxyfunctional polysiloxanes used in the invention, which can be photo-cross-linked

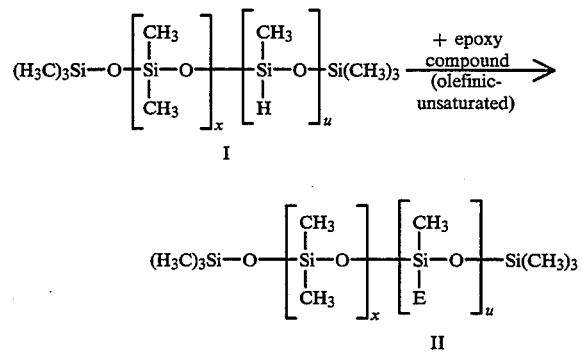

The mass parts of octamethyl cyclotetrasiloxane (OMCTS), SiH-functional polymethyl siloxane with a chain length of n=60 (PMS) and hexamethyl disiloxane (HMDS) as indicated in Table 1 are mixed with 0.2 g trifluoromethane sulfonic acid and 13 drops of distilled water, and stirred at 70° C. for 40 h. After cooling, the reaction mixture is mixed with approximately 1 g $Na_2CO_3$, stirred for 2 h and filtered through a membrane filter with a pore diameter of 1.2 μm under pressure. Volatile constituents are first removed at 100° C./0.1 mbar, and then in a thin-layer evaporator at 120° C./0.1 mbar.

The colorless liquid obtained is dripped into a solution of the amount of freshly distilled epoxide indicated in Table 1, i.e., allyl glycidyl ether (AGE), vinyl cyclohexene oxide (VCHO) or limonene oxide (LO), 0.13 g $H_2PtCl_6.6 H_2O$ and 0.5 ml tert.-butanol in 250 ml toluene, at 70° C., within 6 to 7 h. The reaction mixture is then stirred at 70° C. until a minimum conversion of 95% has been reached (verification by volumetric determination of SiH). To remove the catalyst, 0.2 g cross-linked poly-4-vinyl pyridine is added, then the mixture is stirred at room temperature for 2 h, and filtered under pressure through a membrane filter with a pore diameter of 1.2 μm. The solvent as well as volatile constituents are removed in a vacuum at 70° C./0.1 mbar. Colorless liquids are obtained in almost quantitative yield. Table 1 contains the epoxy values and viscosities determined for characterization of the products.

TABLE 1

| No. | Reaction Components (mass data in g) | | | | | | Polyepoxysiloxane II (chain length n = x + u) | | | | |
| | OMCTS | PMS | HMDS | AGE | VCHO | LO | n | x | u | Epoxy Value [mol/100 g] | Viscosity [mPa · s] |
| --- | --- | --- | --- | --- | --- | --- | --- | --- | --- | --- | --- |
| 1 | 297 | 61 | 5.4 | 142.4 | — | — | 100 | 80 | 20 | 0.21 | 520 |
| 2 | 297 | 61 | 2.7 | 142.8 | — | — | 150 | 120 | 30 | 0.21 | 540 |
| 3 | 297 | 61 | — | 143.2 | — | — | 300 | 240 | 60 | 0.21 | 870 |
| 4 | 297 | 61 | 2.7 | — | 152.4 | — | 150 | 120 | 30 | 0.21 | 550 |
| 5 | 297 | 61 | 2.7 | — | — | 189.8 | 150 | 120 | 30 | 0.19 | 560 |

EXAMPLES 6 TO 8

Production of olefinic-unsaturated, epoxyfunctional polysiloxanes from polysiloxanes containing epoxy groups

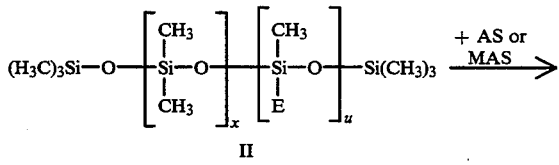

II

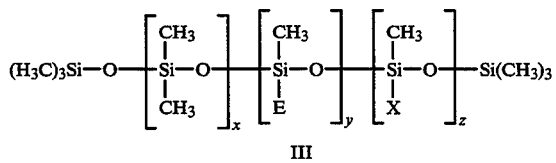

III

The mass parts of the products 1 and 2 given in Table 2 are dissolved in 500 ml water-free toluene under yellow light, with the mass parts of acrylic acid (AS) or methacrylic acid (MAS) also indicated in Table 2, together with 2.5 g diethyl phosphite as the stabilizer and 2.5g N,N,N', N'-tetramethyl-4,4'-diamino diphenyl methane as the catalyst, then stirred at 50° C. for 10 to 11 h. After cooling, the reaction mixture is mixed with acid Al$_2$O$_3$ to remove the catalyst, stirred for 2 h and pressure-filtered through a membrane filter with a pore diameter of 1.2 μm. The solvent and volatile constituents are removed at room temperature, in a vacuum (0.1 mbar). The products obtained are unstable and already gel during further processing or when stored in the refrigerator.

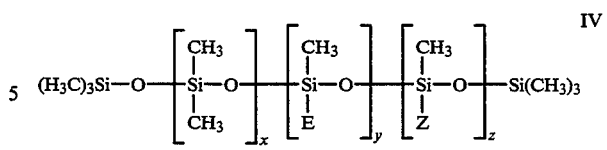

IV

The mass parts of the products 1 to 5 indicated in Table 3 are reacted in toluene, as described in Examples 6 to 8, with acrylic acid or methacrylic acid, 2.5 g diethyl phosphite and 2.5 g N,N,N',N'-tetramethyl-4,4'-diamino diphenyl methane. However, the solution is not concentrated after the catalyst has been removed, but rather mixed with 14.2 g propyl isocyanate and 20 drops of dibutyl tin dilaurate, and stirred at room temperature for 120 h. Then, excess isocyanate is inactivated by adding a few drops of methanol, and then the solvent as well as volatile constituents are removed at room temperature, in a vacuum (0.1 mbar). Colorless clear liquids are obtained in yields between 90 and 100%. Further information relating to the products obtained (epoxy value, acrylate content, viscosity) is summarized in Table 4.

The products must be stored in the refrigerator. An evaluation of the storage stability by weekly determinations of viscosity, which is allowed to increase by a maximum of 5%, yields values of >3 months.

TABLE 3

| | Reaction Components (mass data in g) | | | | | | | Polysiloxane IV (chain length n = x + y + z) | | | |
|---|---|---|---|---|---|---|---|---|---|---|---|
| | Polyepoxysiloxane II | | | | | | | | | | |
| No. | 1 | 2 | 3 | 4 | 5 | AS | MAS | n | x | y | z |
| 9 | 477.3 | — | — | — | — | — | 17.3 | 100 | 80 | 16 | 4 |
| 10 | — | 475 | — | — | — | — | 14.3 | 150 | 120 | 25 | 5 |
| 11 | — | 475 | — | — | — | 12.0 | — | 150 | 120 | 25 | 5 |
| 12 | — | — | 472.6 | — | — | — | 11.4 | 300 | 240 | 52 | 8 |
| 13 | — | — | 472.6 | — | — | — | 8.5 | 300 | 240 | 54 | 6 |
| 14 | — | — | 472.6 | — | — | — | 5.6 | 300 | 240 | 56 | 4 |
| 15 | — | — | — | 482.6 | — | — | 14.5 | 150 | 120 | 25 | 5 |
| 16 | — | — | — | — | 512.5 | 16.8 | — | 150 | 120 | 23 | 7 |

TABLE 4

| | Polysiloxane IV which can be photo-cross-linked | | |
|---|---|---|---|
| No. | Epoxide [mol/100 g] | Acrylate [mol/100 g] | Viscosity [mPa · s] |
| 9 | 0.16 | 0.04 | 2200 |
| 10 | 0.17 | 0.03 | 2400 |
| 11 | 0.17 | 0.03 | 2380 |
| 12 | 0.18 | 0.03 | 3000 |
| 13 | 0.19 | 0.02 | 2850 |
| 14 | 0.20 | 0.01 | 2800 |
| 15 | 0.16 | 0.03 | 2400 |
| 16 | 0.14 | 0.04 | 2500 |

TABLE 2

| | Reaction Components (mass data in g) | | | | Polysiloxane III (chain length n = x + y + z) | | | | | |
|---|---|---|---|---|---|---|---|---|---|---|
| | Polyepoxysiloxane II | | | | | | | | Epoxy value | |
| No. | 1 | 2 | AS | MAS | n | x | y | z | [mol/100 g] | Comment |
| 6 | 477.3 | — | — | 17.3 | 100 | 80 | 16 | 4 | 0.16 | gelling when stored in refrigerator |
| 7 | — | 475 | — | 14.3 | 150 | 120 | 25 | 5 | not determinable | gelling when processed |
| 8 | — | 475 | 12.0 | — | 150 | 120 | 25 | 5 | not determinable | gelling when processed |

EXAMPLES 9 TO 16

Production of the epoxyfunctional polysiloxanes according to the invention, which can be photo-cross-linked

EXAMPLE 17

Production of Polysiloxane/Enzyme Layers 100 parts by mass of an epoxyfunctional polysiloxane with the structure

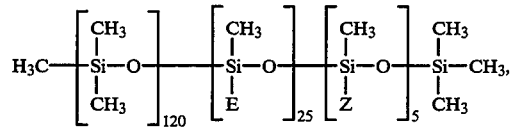

with E = 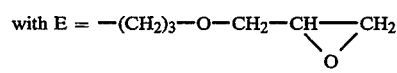

and Z = 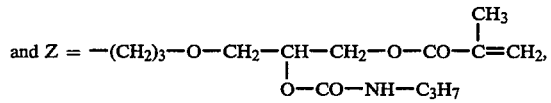

are mixed with 7 parts by mass propoxylated glycerol triacrylate as the reactive diluent and 2 parts by mass 2-hydroxy-2-methyl-1-phenyl propan-1-one as the photoinitiator, and mixed with a corresponding amount of toluene to adjust the desired processing properties. This solution is then applied to the sensitive surface of a sensor, which has been pretreated with an adhesion agent, if necessary, by dipping, dripping or spreading. Parallel to this, silicon wafers are coated with the same solution, using a varnish centrifuge; the centrifuge time is approximately 10 s.

The layers are dried in a laminar box and subsequently cross-linked under nitrogen, by UV irradiation (System F 450 of the company Fusion UV-Curing Systems) in a wavelength range of 200 to 450 nm; irradiation period: 3.2 s. To remove soluble components, the cross-linked layers are extracted with dioxane for 24 h, at room temperature. To increase the hydrophilicity of the layers, part of the epoxy groups is reacted with compounds containing NH groups, in the form of amino acids. In this connection, storage of the layers in a 2% solution of proline or glutaminic acid in a 2:1 mixture of dioxane and water at 40° to 60° C. has particularly proven to be effective. Using silicon wafers treated in a corresponding manner, the conversion can be followed by IR spectroscopy. A conversion of 50% is sufficient in most cases; if needed, however, higher values can also be adjusted.

Immobilization of the enzymes takes place by incubation of the layers in an approximately 1 to 2% solution of the enzyme in water at 20° to 30° C. To accelerate this process, the solution can be mixed with 10 to 50% dioxane, depending on the sensitivity of the enzyme. Immobilization is complete after 1 to 8 h. Remaining epoxy groups can be eliminated by gentle conversion with amino acids. As the last step, the layers are freed from extractable components by being intensively washed with water.

Table 5 contains a summary of the enzymes immobilized according to the invention, in identically pretreated layers with a thickness of 10 μm, on silicon wafers, immobilized at 30° C. within 4 h, as well as the enzyme activity at 25° C.

TABLE 5

| Enzyme | Activity | Determination Method |
|---|---|---|
| Glucose oxidase from *Aspergillus niger*, lyophil. 240 U/mg | 1.2 U/cm$^2$ | Gluc-DH Method of the Merck company |
| Catalase from cattle liver, suspension 65,000 U/mg | 550 U/cm$^2$ | See: B. Stellmach, "Bestimmungsmethoden Enzyme", Steinkopff-Verlag, Darmstadt 1988, pages 152 to 155 |
| Urease from broad beans, lyophil. 100 U/mg | 1.0 U/cm$^2$ | See: B. Stellmach, "Bestimmungsmethoden Enzyme", Steinkopff-Verlag, Darmstadt 1988, pages 269 to 271 |
| Alcohol dehydrogenase from yeast, lyophil. 400 U/mg | 3.2 U/cm$^2$ | See: B. Stellmach, "Bestimmungsmethoden Enzyme", Steinkopff-Verlag, Darmstadt 1988, pages 11 and 12 |
| L-asparaginase, 50% solution in glycerol 80 U/mg solution | 0.8 U/cm$^2$ | See: B. Stellmach, "Bestimmungsmethoden Enzyme", Steinkopff-Verlag, Darmstadt 1988, pages 63 to 68 |

"Bestimmungsmethoden Enzyme" = "Determination Methods for Enzymes"

EXAMPLE 18

Evaluation of the Functional Stability of the Immobilized Enzymes

To evaluate the functional stability of enzymes immobilized according to the invention (duration: 4 h), the activities of the layers with a thickness of 10 μm, produced according to Example 17 on silicon wafers, was measured at 25° C. over a period of several weeks (see Table 5 in this regard). The activity of glucose oxidase was followed for 70 days, without any reduction in the initial value being found. Parallel to this, the activity decrease of an aqueous glucose oxidase solution was determined at 20° C., according to the determination method indicated in Table 5. This showed an activity loss of approximately 50% within 10 days, which documents the greater stability of the glucose oxidase immobilized according to the invention. An evaluation of the other immobilized enzymes listed in Table 5 yields the result that the initial activity value measured was maintained for at least 8 weeks.

EXAMPLE 19

Evaluation of the Functional Stability of Biosensors with Immobilized Enzymes According to the Invention Polysiloxane/enzyme layers are produced on sensor measurement arrangements, according to the method described in Example 17, and their function and functional stability is followed by measurement of the resulting sensor signal. Table 6 contains the enzymes evaluated, as well as the measurement arrangement selected for the evaluation, and the useful lifetime.

TABLE 6

| Enzyme | Sensor Measurement Arrangement | Useful Lifetime |
|---|---|---|
| Glucose oxidase (GOD) | oxygen sensor according to EP-OS 0 470 473 | >8 weeks |
| GOD + catalase (1:1) | oxygen sensor according to EP-OS 0 470 473 | >8 weeks |
| Urease | NH$_4$$^+$-sensitive glass electrode (company: Tecan AG) | >8 weeks |
| L-asparaginase | NH$_4$$^+$-sensitive glass electrode (company: Tecan AG) | >8 weeks |

What is claimed is:

1. A biosensor prepared by a method comprising the steps of:

applying an olefinic-unsaturated, epoxyfunctional polysiloxane to a carrier material in the form of a layer, the polysiloxane having the following structure:

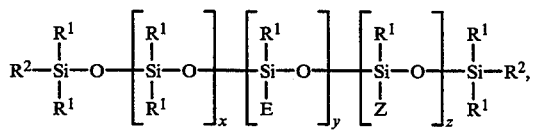

where the following applies:

E =

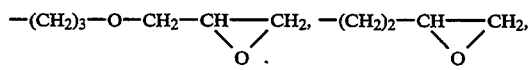

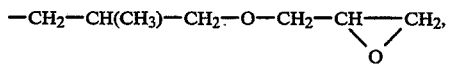

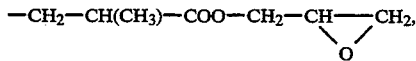

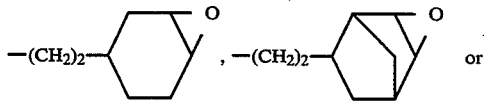 or

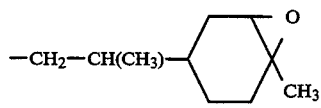

Z = a vinyl group or a photopolymerizable group with 8 to 40 C. atoms, which is obtained by addition of a photopolymerizable compound to E, and subsequent addition of an aliphatic, cycloaliphatic or aromatic monoisocyanate or monoisothiocyanate with 2 to 10 C. atoms to the secondary OH group formed upon opening of the epoxide ring, $R^1$ = alkyl with 1 to 4 C. atoms or phenyl, $R^2 = R^1$, E or Z, where $R^1$ and $R^2$ can be the same or different in each instance, x = 50 to 1000, y = 10 to 300, z = 3 to 8, cross-linking the polysiloxane by means of high-energy radiation to form an epoxyfunctional cross-linked polysiloxane polymer matrix, treating the layer with an aqueous solution of a biochemical substance having groups that covalently react with the epoxy groups of the polysiloxane, whereby the biochemical substance is immobilized in the polymer matrix by reaction with epoxy groups, and stabilizing the layer by reaction of any non-reacted epoxy groups remaining after the step of treating with a compound containing an amino group, a carboxyl group or an amino group and a carboxyl group.

2. The biosensor according to claim 1 wherein the cross-linked polysiloxane is hydrophilized before immobilization of the biochemical substance by reacting some of the epoxy groups of the polysiloxane with a hydrophilic compound containing a reactive group.

3. The biosensor according to claim 1 wherein the biochemical substance is an enzyme.

* * * * *